United States Patent [19]

Miki et al.

[11] 4,082,780
[45] Apr. 4, 1978

[54] ESTRADIOL DERIVATIVES

[75] Inventors: Takuichi Miki, Amagasaki; Kentaro Hiraga, Nagaokakyo; Giichi Goto, Takatsuki, all of Japan

[73] Assignee: Takeda Chemical Industries, Ltd., Osaka, Japan

[21] Appl. No.: 744,185

[22] Filed: Nov. 22, 1976

[30] Foreign Application Priority Data

Nov. 27, 1975   Japan ................................ 50-142509

[51] Int. Cl.² .............................................. C07J 1/00
[52] U.S. Cl. .................................................. 260/397.5
[58] Field of Search ....................... 260/397.5 A, 397.5

[56] References Cited

U.S. PATENT DOCUMENTS 4,022,892   5/1977   Kanojia .............................. 260/397.5

FOREIGN PATENT DOCUMENTS 1,096,732   2/1964   United Kingdom ............... 260/397.5

OTHER PUBLICATIONS

Chem. Abstracts, vol. 67, (1967), Par. 11,670C.

*Primary Examiner*—Elbert L. Roberts
*Attorney, Agent, or Firm*—Burgess, Ryan and Wayne

[57] ABSTRACT

Novel estradiol derivatives of the formula

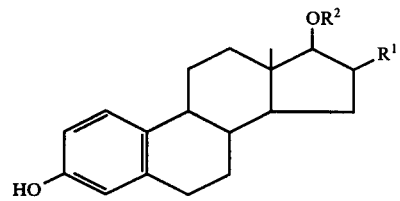

wherein $R^1$ means an alkyl group of two or more carbon atoms, and $R^2$ is hydrogen or an acyl group, have antiestrogen activity and are useful as antiestrogen drugs.

15 Claims, No Drawings

ESTRADIOL DERIVATIVES

The present invention relates to novel and useful 16β-alkylestradiol derivatives and to a process for producing the same.

More particularly, the present invention relates to 16β-alkylestradiols represented by the formula (I):

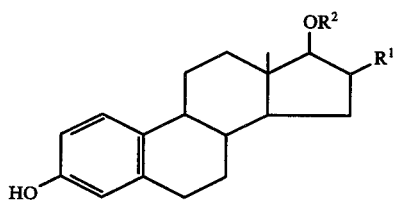

wherein $R^1$ means an alkyl group of two or more carbon atoms, and $R^2$ is hydrogen or an acyl group, and to a process for producing the same.

Hitherto, testosterone or derivatives thereof (e.g. testosterone propionate) have been used for the therapy of estrogen-dependent diseases (e.g. advanced breast cancer) as an antiestrogen drug. However the therapy is generally accompanied by the side effect of inducing masculine characteristics resulting from the androgenic potency of testosterone which leads the patient to discontinue the therapy.

Under the circumstances, the present inventors studied and discovered that 16β-alkylestradiol derivatives have substantially no estrogen activity but rather than antiestrogen activity and that this propensity is particularly pronounced where the number of carbon atoms in the 16β-alkyl moiety is within the range of 2 to 4. The present invention is accomplished on the basis of the above findings.

The principal object of the present invention is to provide a compound of the general formula (I), which is useful as an antiestrogen drug, and another object of the invention is to provide a process for producing the compound (I).

Referring to the formula (I) and formula (II) described hereinafter, the alkyl group of two or more carbon atoms as designated by $R^1$ may be straight-chain or branched, and saturated or unsaturated, thus being exemplified by lower alkyl groups having 2 to 4 carbon atoms, such as ethyl, propyl, isopropyl, butyl, isobutyl, sec-butyl, tert-butyl, allyl, 3-butenyl and so on. The acyl group as designated by $R^2$, $R^{2'}$ and $R^3$ is a hydrocarbon-carbonyl group whose hydrocarbon moiety has 1 to 8 carbon atoms. The hydrocarbon-carbonyl group is exemplified by lower alkylcarbonyl groups whose alkyl moieties have 1 to 3 carbon atoms, e.g. acetyl, propionyl, butyryl, etc.; arylcarbonyl groups, e.g. benzoyl; and aralkylcarbonyl groups, e.g. phenylpropionyl, etc. Where $R^2$ or $R^{2'}$ is an acyl group, the substituent —$OR^2$ or —$OR^{2'}$ in 17-position of formula (I) or (II) is an esterified hydroxyl group, and the corresponding compound is an 17-ester of compound (I) or (II). The hydrocarbon residue as designated by $R^3$ in the formula (II) is an alkyl, aryl and aralkyl groups. The alkyl group mentioned for $R^3$ may be a straight-chain or branched lower alkyl group of 1 to 3 carbon atoms such as methyl, ethyl, propyl, isopropyl or the like; the aryl group also mentioned for $R^3$ may for example be phenyl or p-nitrophenyl; and the aralkyl group for $R^3$ may for example be benzyl or benzhydryl.

The compounds (I) of the present invention can be produced according to a known method. For example, the compounds (I) are produced according to the method illustrated as follows;

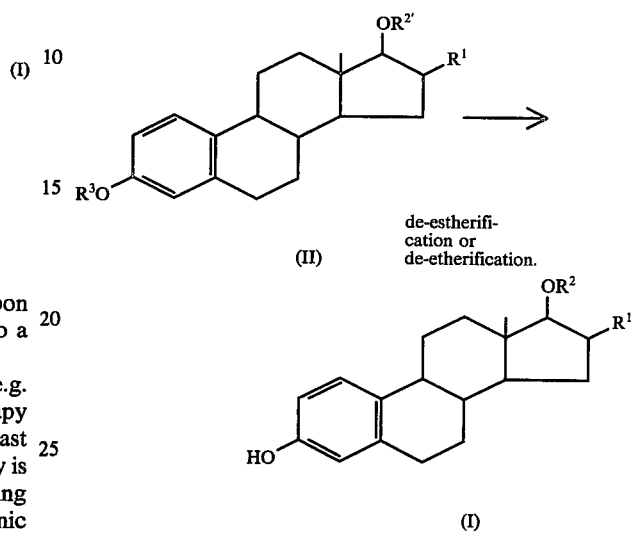

wherein $R^1$ and $R^2$ have the same meaning as defined above, $R^{2'}$ is hydrogen or an acyl group, and $R^3$ is a hydrocarbon residue or an acyl group. Namely, the above method is carried out by subjecting the compound (II) to a reaction leading to a cleavage of an acyl group or hydrocarbon residue of the esterified or etherified hydroxyl group in 3-position thereof.

By the present reaction, the acyl group or hydrocarbon residue of the esterified or etherified hydroxyl group in the 3-position is removed, thus leaving a free hydroxyl group in the 3-position. The hydrocarbon residue may be, for instance, alkyl having 1 to 3 carbon atoms, phenyl, p-nitrophenyl, benzyl, or benzhydryl. The acyl group may be, for instance, a lower alkylcarbonyl group whose alkyl moiety has 1 to 3 carbon atoms or an arylcarbonyl group.

This reaction, where $R^3$ is an alkyl or aryl group, that is to say where —$OR^3$ is an etherified hydroxyl group, is carried out by reacting the compound (II) with a reagent capable of cleaving an ether linkage. This ether-cleaving reagent may be any reagent that is able to cleave the ether linkage of the etherified hydroxyl group in the 3-position without affecting the steroid skeleton and the 16β-alkyl group of the starting compound. Thus, for example, there may be mentioned acidic reagents, for example, hydrohalogenic acids such as hydrochloric acid, hydrobromic acid, hydroiodic acid, etc., halides of phosphorus, boron, aluminum, thallium and titanium, etc., preferably the corresponding chlorides and bromides (e.g. phosphorus tribromide, boron tribromide, aluminum chloride, titanium tetrachloride, etc.), pyridinium halide (e.g. pyridinium chloride); Grignard's reagents (e.g. methylmagnesium iodide, ethylmagnesium bromide); sodium iodide-dimethylsulfoxide and so forth. Generally, such ether-cleaving reagents are used in amounts within the range of about 1 to 10 moles per mole of the compound (II). While the reaction takes place in the absence of a solvent, the reaction is generally carried out in the presence of a solvent. As said solvent may be mentioned an organic solvent capable of dissolving steroid compounds, such as ethers (e.g. diethylether, tetrahydrofuran, etc.), halogenated hydrocarbons (e.g. dichloromethane, chloroform, chlorobenzene, dichloroethane, trichloroethylene, etc.), esters (e.g. ethyl acetate, butyl acetate, etc.), nitrobenzene, dimethylformamide, dimethylsulfoxide, hexamethylphosphoramide and so on. The reaction is generally conducted within the temperature range of −10° to 250° C when no solvent is employed, or at temperatures between −10° C and the boiling point of the solvent employed when a solvent is employed. Following the reaction, the reaction mixture may be immediately treated with water to recover the contemplated compound. Where $R^3$ is an aralkyl group, the cleavage reaction according to this invention is carried out by subjecting the compound (II) to catalytic reduction or hydrolysis. The catalytic reduction is carried out by means of a catalyst such as platinum oxide, palladium, Raney nickel or the like, generally in a solvent such as methanol, ethanol, ether or tetrahydrofuran at a temperature between about 10° and 60° C and at a pressure within the range of 1 to 100 kg/cm². Where $R^1$ is an unsaturated alkyl group, the conditions should be selected from, among the above, such that the unsaturated bond will not be reduced, e.g. reduction at normal temperature and atmospheric pressure. The hydrolysis is carried out with the same reagent as the ether-cleavage reagent to be employed where $R^3$ is an alkyl or aryl group, or with a halogenoacetic acid such as trifluoroacetic acid, trichloroacetic acid or monochloroacetic acid under the same conditions as those employed for the ether-cleavage reaction where $R^3$ is an alkyl or aryl group (e.g. as to the solvent, reaction temperature and other parameters).

Where $R^3$ is an acyl group, that is where —$OR^3$ is an esterified hydroxyl group, the cleavage reaction according to this invention is carried out by subjecting the compound (II) to hydrolysis. This hydrolysis may be conducted by any procedure that enables us to cleave the ester linkage of the esterified hydroxyl group in the 3-position without affecting the steroid skeleton or the 16β-alkyl group of starting compound (II). Thus, for example, the hydrolysis is conducted generally in a solvent. The solvent is a mixture of water and a solvent such as an alcohol (e.g. methanol, ethanol, t-butanol, n-propanol or the like), ether, ethyl acetate, tetrahydrofuran, dimethylsulfoxide or dimethylformamide. The hydrolysis is conducted by means of an inorganic or organic basic reagent such as an alkali metal hydroxide (e.g. sodium hydroxide, potassium hydroxide, sodium carbonate, potassium carbonate, sodium hydrogen carbonate, potassium hydrogen carbonate, etc.), triethylamine, triethylenediamine or the like, or an acid reagent such as an inorganic acid (e.g. hydrochloric acid, sulfuric acid, nitric acid, phosphoric acid, etc.) or an organic acid (e.g. formic acid, acetic acid, oxalic acid, p-toluenesulfonic acid, etc.). The reaction is generally conducted at a temperature within the range of 0° to about 80° C.

Where both $R^{2'}$ and $R^3$ of starting compound (II) are acyl groups, both esterified hydroxyl group in the 3- and 17-positions thereof are generally hydrolyzed to free hydroxyl groups, but if desired, the substituent in the 3-position of compound (II) may be selectively hydrolyzed to convert the esterified hydroxyl group in the 3-position alone to a free hydroxyl group by selecting a mild set of hydrolyzing conditions, for example at a comparatively low temperature, e.g. room temperature, using a weakly basic reagent such as an alkali metal carbonate or alkali metal hydrogen carbonate. Compound (I) may also be produced by subjecting Compound (II) wherein $R^{2'}$ is an acyl group to Birch's reduction, for example.

Following the cleavage reaction of this invention, the contemplated end compound (I) may be isolated and purified by procedures conventional per se (e.g. treatment with water, extraction, concentration, recrystallization, chromatography, etc.).

The thus produced compounds (I) have antiestrogen activity, i.e. the inhibitory activity on the binding of estradiol to the estradiol-receptor protein isolated from the uterine tissues, and have substantially no estrogen activity and no androgen activity. Further the present compounds (I) are low in toxicity, and therefore, they are of use as antiestrogen drugs for the alleviation of highly estrogen-dependent diseases (e.g. functional uterine hemorrhage, mastitis, etc.) in said mammalian animals including mouse, rat and man.

For example, the 16β-ethylestradiol has an antiestrogen activity several times as potent as that of clomiphene and of testosterone, and can be used as an antiestrogen drug for said mammals including mouse, rat and man in the same usage manner as testosterone for alleviation of the above diseases.

Compounds (I) except 16β-ethylestradiol may also be employed, depending on the potency of their antiestrogen activity, as antiestrogen drugs in the same usage manner as testosterone for alleviation of the above disease.

Where the compound (I) is employed as an antiestrogen drug, it may be orally or parenterally administered as it is or in admixture with a known excipient or carrier (e.g. lactose, calcium phosphate, corn starch, methyl cellulose, coconut oil, sesame oil, peanut oil, etc.) in such dosage forms as tablets, capsules, powders, suspensions or injections.

These injections are prepared, for example, by dissolving or suspending the compounds (I) in vegetable oils (e.g. sesame oil, cottonseed oil, castor oil, olive oil, corn oil, peanut oil, etc.) in combination, if desired, with antiseptics (e.g. benzyl alcohol, benzyl benzoate, chlorobutanol, etc.), solubilizing agents, surface active agents, etc. Among the compounds (I), 17β-ester derivatives are readily soluble in oils and exhibit relatively sustained anti-estrogenic action. When the compounds (I) are administered orally, they may be as powders, tablets, capsules, pills, liquids, syrups, elixirs, buccals, granules, etc. Some examples of prescription in which the compounds of this invention are utilized as antiestrogen drugs are as hereinafter.

For example, where the compound (I) is administered parenterally as an antiestrogen drug for alleviation of breast cancer, the intramuscular dose range is between 10 and 400 mg, more preferably between 30 and 100 mg for an adult female human per week. The dose may be divided into 2 to 3 weekly doses of corresponding smaller amounts.

The compound (I) wherein $R^2$ is an acyl group, i.e. the 17-ester of 16β-alkyl estradiol (I) is, generally speaking, long-active, slow-active, stable in storage and/or easy to prepare dosage forms thereof in comparison with the 17-hydroxyl compound corresponding thereto.

There may be exemplified compositions in which a compound of this invention is used an antiestrogen drug;

| Injections: | (1) 16β-ethylestradiol sesame oil | 10 weight parts 1000 volume parts |
| --- | --- | --- |
| | (2) 16β-ethylestradiol 17-acetate benzyl benzoate sesame oil | 100 weight parts 20 volume parts 1000 volume parts |

| Capsules: | 16β-ethylestradiol 17-acetate | 20 weight parts |
| --- | --- | --- |
| | lactose | 140 weight parts |
| | corn starch | 50 weight parts |
| | sugar ester | 4 weight parts |
| | calcium salt of carboxy-methylcellose | 4 weight parts |
| | magnesium stearate | 2 weight parts |
| | | (220 mg/capsul) |

| Tablets: | 16β-ethylestradiol 17-acetate | 20 weight parts |
| --- | --- | --- |
| | lactose | 100 weight parts |
| | corn starch | 90 weight parts |
| | sugar ester | 4 weight parts |
| | calcium salt of carboxymethyl-cellose | 4 weight parts |
| | magnesium stearate | 2 weight parts |
| | | (220 mg/tablet.) |

In the prescriptions, "weight part" corresponds the "gram", and "volume part" corresponds to "milliliter".

The starting compound (II) for this invention may be produced by the method described in the specification of German Patent Application Laid-Open No. 2100319.0, or by the method described in Chemical Pharmaceutical Bulletin Vol.21, 1393(1973), or a method analogous with such methods as above, from the estra-1,3,5(10)-trien-16-oxo-17β-ols corresponding to the compound (II) or the compounds described in Tetrahedron Vol.30, 2107(1974). It should be noted that, generally, said estra-1,3,5(10)-trien-16-oxo-17β-ols or their derivatives may be produced by procedures similar to the procedures established for the species known among them.

The starting compound (II), wherein both $R^{2'}$ and $R^3$ are the same acyl group, can be produced by reacting the compound (I) wherein $R^2$ is hydrogen with an acylating agent according to per se known procedures established for acylation of alcoholic hydroxyl group. The acylating agent is exemplified by acid anhydrides (e.g. acetic anhydride, propionic anhydride, phenylpropionic anhydride)-organic or inorganic bases, acid halides (e.g. acetyl chloride, propionyl chloride, phenylpropionyl chloride, benzoyl chloride)-organic or inorganic bases, acids-dehydrating agents such as sulfuric acid, hydrochloric acid, dicyclohexylcarbodiimide, etc. For example, the acylating reaction is conducted in the presence of a catalyst which may be an alkaline catalyst such as, for example, pyridine, picolin, collidine, quinoline or a tertiary amine, e.g. triethylamine, or an acid catalyst such as; for example, a Lewis acid, e.g. boron trifluoride, zinc chloride or aluminum chloride, p-toluene sulfonic acid or potassium hydrogen sulfate. The raction is generally conducted in one of the common protoninert solvents for steroids which include, among others, halogenated hydrocarbons, e.g. chloroform, dichloromethane, etc., hydrocarbons, e.g. toluene, benzene, hexane, etc., esters, e.g. ethyl acetate etc., dimethyl formamide, pyridine, picoline, etc. Alternatively, use may be made of a large excess of the acylating agent such as organic acid anhydride or the like so that the acylating agent will also function as the nesary solvent. The reaction usually proceeds at 0° C to room temperature, although the reaction may be hastened by heating the system to the neighborhood of 100° C. After the reaction is complete, the reaction mixture may for example be treated with a large quantity of water so as to let the acyloxy derivatives crystallize or, alternatively, to subject to the extraction with an organic solvent to obtain the compound.

EXAMPLE 1

To 1 g of 16β-ethylestradiol 3-methyl ether is added 1.3 g of pyridinium chloride and the mixture is heated at 150° C. After 2 hours, the reaction mixture is poured into ice-water and the resultant crystals are collected by filtration. Recrystallized from ethyl acetate, 16β-ethylestradiol is obtained as needles melting at 173° to 174° C.

IR $\nu_{max}^{KBr}$ cm$^{-1}$: 3410, 3150(OH), 1610, 1595(Ar, "Ar" means "Aryl").

NMR $\delta_{ppm}^{d_6\text{-}DMSO}$: 0.68(3H,s,18-CH$_3$), 1.11(3H,t,J=6Hz, CH$_3$), 3.57(1H,d,J=9Hz,17α-H),6.4-7.2(3H,m,Ar). Mass m/e 300(M$^+$), 282, 213.

Elemental analysis, for C$_{20}$H$_{28}$O$_2$: Calcd: C, 79.95; H, 9.39. Found: C, 79.89; H, 9.24.

EXAMPLE 2

To a solution of 2.3 g of 16β-ethylestradiol 3-methyl ether in 25 ml of ether is added an ethereal solution of methylmagnesium iodide (prepared by reacting 1.2 g of magnesium with 7.0 g of methyl iodide in 50 ml of ether). The resultant mixture is gently heated and the ether is gradually removed under reflux. Following removal of ether, the reaction mixture is further heated at 120° C for 2 hours. After cooling, the residue is carefully poured into ice-water in a small portion. The aqueous mixture is adjusted to pH 2 with 5N-hydrochloric acid and the resultant crystals are collected by filtration. Recrystallized from ethyl acetate, 16β-ethylestradiol is obtained as needles. In melting point and IR spectrum, this product is in agreement with the product obtained in Example 1.

EXAMPLE 3

In 10 ml of methanol is dissolved 360 mg of 16β-ethylestradiol 3,17-diacetate(melting point: 148° to 149° C), followed by the addition of 2N-methanolic solution of potassium hydroxide. The mixture is heated at 50° C for 3 hours. After cooling, water is added to the reaction mixture, and the resultant mixture is then adjusted to pH 2 with 5N-hydrochloric acid. The separated crystals are recovered by filtration to yield 16β-ethylestradiol. In melting point and IR spectrum, this compound is in agreement with the product obtained in Example 1.

EXAMPLE 4

(1) To a solution of 0.17 g of 16β-ethylestradiol in 5 ml of pyridine is added 1 ml of acetic anhydride. After keeping the resultant mixture at 50° C for 8 hours, 10 ml of water is added to the reaction mixture, and the mixture is extracted with dichloromethane. The organic layer is washed with water, dried over anhydrous sodium sulfate and concentrated, whereupon pale yellow crude crystals are obtained. Recrystallization from methanol gives 16β-ethylestradiol 3,17-diacetate as colorless needles melting at 148° to 149° C.

IR $\nu_{max}^{KBr}$ cm$^{-1}$: 1760(OCOCH$_3$), 1725(OCOCH$_3$).

(2) To a solution of 0.25 g of 16β-ethylestradiol 3,17-diacetate in 15 ml of methanol is added a solution of 19 mg of anhydrous potassium carbonate in 2 ml of methanol and the mixture is stirred at room temperature for 15 minutes. The reaction mixture is concentrated under reduced pressure and made acidic with 2N-hydrochloric acid, whereupon crystals separate.

Recrystallized from ether-n-hexane(1:1), 16β-ethylestradiol 17-acetate is obtained as colorless needles melting at 187° to 188° C.

IR $\nu_{max}^{KBr}$ cm$^{-1}$: 3400(OH), 1725(OCOCH$_3$).

Elemental analysis, for $C_{22}H_{30}O_3$: Calcd. C, 77.15; H, 8.83. Found C, 77.19; H, 8.80.

EXAMPLE 5

(1) 16-Ketoestradiol 3-benzylether is reacted with ethyl magnesium iodide in ether to give 16β-hydroxy-16α-ethylestradiol 3-benzylether. The product is treated with pyridine-acetic anhydride to give 16β-hydroxy-16α-ethylestradiol 17-acetate. The resultant 17-acetate is heated with zinc powder in toluene at 130° C for 5 hours to give 16β-ethylestrone 3-benzylether. The product is treated with sodium borohydride in methanol, whereupon 16β-ethylestradiol 3-benzylether is produced.

(2) In 30 ml of methanol is dissolved 0.73 g of 16β-ethylestradiol 3-benzyl ether, followed by addition of 210 mg of platinum oxide. The catalytic reduction is thus conducted at atmospheric pressure and room temperature. After the absorption of hydrogen has completed, the platinum oxide is filtered off and the filtrates are concentrated under reduced pressure. By the above procedure is obtained 16β-ethylestradiol as crude crystals. This crude product is recrystallized from ethyl acetate as in Example 1. In melting point and IR spectrum, this product is in agreement with the product obtained in Example 1.

EXAMPLE 6

To a solution of 0.93 g of 16β-isopropylestradiol 3-methyl ether in 15 ml of ether is added an ethereal solution of methylmagnesium iodide. The mixture is then treated in the same manner as Example 2, whereupon 16β-isopropylestradiol is obtained as crude crystals. The resultant crude crystals are recrystallized from ethyl acetate. Melting point: 221° to 222° C.

IR $\nu_{max}^{KBr}$ cm$^{-1}$: 3400(OH), 1610, 1590(Ar).

NMR δ $_{ppm}^{d_6-DMSO}$: 0.70(3H,s,18-CH$_3$), 0.83(3H,d,J=5Hz,CH$_3$), 0.98(3H,d,J=5Hz,CH$_3$), 3.73(1H,d,J=9Hz,17α-H), 6.4-7.2 (3H,m,Ar).

Elemental analysis, for $C_{21}H_{30}O_2$: Calcd. C, 80.21; H, 9.62. Found C, 80.30; H, 9.67.

EXAMPLE 7

Under ice-cooling, 0.2 g of phosphorus tribromide is added in a small portion to a solution of 0.6 g of 16β-ethylestradiol 3-methyl ether in 10 ml of dichloromethane. The resultant mixture is allowed to stand at room temperature for 4 hours. The reaction mixture is poured in a small portion into ice-water and extracted with dichloromethane. Upon removal of the solvent by concentration, 16β-ethylestradiol is obtained as crude crystals. Recrystallization under the same conditions as Example 1 yields pure crystals. In melting point and IR spectrum, this product is in agreement with the product obtained in Example 1.

In the similar manner as above, 16β-allylesteradiol is obtained from 16β-allylestradiol 3-methyl ether. Melting point: 204° to 206° C.

IR $\nu_{max}^{KBr}$ cm$^{-1}$: 3350(OH), 3080, 1640(allyl), 1610, 1595(Ar).

Elemental analysis, for $C_{21}H_{28}O_2$ Calcd. C, 80.73; H, 9.03. Found C, 80.77; H, 9.10.

EXAMPLE 8

(1) To a solution of 0.3 g of 16β-ethylestradiol in 2 ml of pyridine is added 0.6 ml of propionic anhydride. After keeping the resultant mixture at 50° C for 10 hours, 10 ml of water is added to the reaction mixture, followed by extraction with dichloromethane. The organic layer is washed with water, dried over anhydrous sodium sulfate and concentrated, whereupon crude crystals are obtained. Recrystallization from methanol gives 16β-ethylestradiol 3,17-dipropionate as colorless needles melting at 57° C.

IR $\nu_{max}^{KBr}$ cm$^{-1}$: 1760(OCOC$_2$H$_5$), 1725(OCOC$_2$H$_5$).

(2) To a solution of 0.2 g of 16β-ethylestradiol 3,17-dipropionate in 10 ml of methanol is added 16 mg of anhydrous potassium carbonate, followed by stirring at room temperature for 30 minutes. The reaction mixture is concentrated under reduced pressure, and the residue is made acidic with 2N-hydrochloric acid, whereupon crystals are obtained. The crystals are collected by filtration and recrystallized from hexane to give 16β-ethylestradiol 17-propionate as colorless needles melting at 176° to 178° C.

IR $\nu_{max}^{KBr}$ cm$^{-1}$: 3350(OH), 1700(OCOC$_2$H$_5$).

Elemental analysis for $C_{23}H_{32}O_3$: Calcd. C, 77.49; H, 9.05. Found C, 77.48; H, 9.07.

EXAMPLE 9

(1) In a similar manner to Example 4-(1), 16β-isopropylestradiol 3,17-diacetate is obtained by acetylation of 16β-isopropylestradiol with acetic anhydride-pyridine. Melting point: 115° to 116° C. IR $\nu_{max}^{KBr}$ cm$^{-1}$: 1765(OCOCH$_3$), 1735(OCOCH$_3$).

(2) According to a similar manner to Example 4-(2), 16β-isopropylestradiol 3,17-diacetate is hydrolized with anhydrous potassium carbonate to give 16β-isopropylestradiol 17-acetate. Melting point: 193° to 194° C. IR $\nu_{max}^{KBr}$ cm$^{-1}$: 1350(OH), 1700(OCOCH$_3$).

Elemental analysis for $C_{23}H_{32}O_3$: Calcd. C, 77.49; H, 9.05. Found C, 77.31; H, 9.11.

EXAMPLE 10

(1) To a solution of 0.2 g of 16β-ethylestradiol 3-methylether 17-acetate in 10 ml of dimethylsulfoxide is added 0.5 g of dried sodium iodide, and the mixture is refluxed for 3 hours under nitrogen gas stream. After cooling, 30 ml of water is added to reaction mixture, and the resultant mixture is extracted with ether. The ether layer is washed with water, dried over anhydrous sodium sulfate and concentrated, whereupon pale yellow crude crystals are obtained. Recrystallization from ether-hexane (1:1) gives 16β-ethylestradiol 17-acetate. This product is in accordance with the product obtained in Example 4 in melting point and IR spectrum.

(2) According to a similar manner to Example 7, 16β-ethylestradiol 3-methylether 17-acetate is treated with phosphorus tribromide to give 16β-ethylestradiol 17-acetate.

EXAMPLE 11

(1) To a solution of 0.3 g of 16β-ethylestradiol in 10 ml of pyridine is added 0.5 g of 3-phenylpropionyl chloride, and the mixture is kept at room temperature for 12 hours. To the reaction mixture is added 10 ml of ice-water, and the mixture is extracted with ether. The ether layer is washed with 3N-aqueous solution of potassium carbonate, dried over anhydrous sodium sulfate and concentrated, whereupon 16β-ethylestradiol 3,17-diphenylpropionate is obtained.

IR $\nu_{max}^{Neat}$ cm$^{-1}$: 1760, 1735(OCOCH$_2$CH$_2$-C$_6$H$_5$).

(2) To a solution of the product obtained in the above experiment (1) in 10 ml of methanol is added 0.1 g of potassium carbonate and the mixture is stirred at room temperature for 30 minutes. The reaction mixture is concentrated, and to the resultant residue is added 10 ml of water, followed by extraction with ether. The ether layer is washed with water, dried over anhydrous sodium sulfate and concentrated, whereupon crude oily product is obtained. The product is subjected to silica gel column chromatography using benzene-ether(3:1) as an eluent thereof to give 16β-ethylestradiol 17-phenylpropionate as colorless oil. IR : $\nu_{max}^{Neat}$ cm$^{-1}$: 3400(OH), 1700(OCOCH$_2$CH$_2$C$_6$H$_5$), 1605(Ar). Mass: m/e 432(M$^+$, M=432 for C$_{29}$H$_{36}$O$_3$) 404(-28), 299(-133).

EXAMPLE 12

(1) In a similar manner to Example 11-(1), 16β-ethylestradiol is reacted with benzoyl chloride to give crude crystals. Recrystallization from ether gives 16β-ethylestradiol 3,17-dibenzoate melting at 177° to 178° C. IR $\nu_{max}^{KBr}$ cm$^{-1}$: 1735, 1720(OCOC$_6$H$_5$).

(2) According to a similar manner to Example 11-(2), 16β-ethylestradiol 3,17-dibenzoate is hydrolyzed with potassium carbonate to give 16β-ethylestradiol 17-benzoate melting at 194 to 196° C. IR $\nu_{max}^{KBr}$ cm$^{-1}$: 3450(OH), 1695(OCOC$_6$H$_5$).

Elemental analysis for C$_{27}$H$_{32}$O$_3$ Calcd. C, 80.16; H, 7.97. Found C, 79.87; H, 7.99.

EXAMPLE 13

(1) 16-Ketoestradiol 3-methylether is reacted with n-butylmagnesium iodide to give 16β-hydroxy-16β-n-butylestradiol:

IR $\nu_{max}^{Neat}$ cm$^{-1}$: 3500(OH), 1605, 1590(Ar). Acetylation of the compound with acetic anhydride in pyridine gives the corresponding 17-acetate:

IR $\nu_{max}^{KBr}$ cm$^{-1}$: 3450(OH), 1730(OCOCH$_3$), 1605, 1595(Ar).

The 17-acetate is treated with zinc powder in toluene for 4 hours at 130° C to give 16β-butylestrone 3-methyl ether:

IR $\nu_{max}^{Neat}$ cm$^{-1}$: 1735(c=o), 1605, 1595(Ar), Reduction of 16β-butylestrone 3-methyl ether with sodium borohydride in methanol gives 16β-n-butylestradiol 3-methylether:

IR $\nu_{max}^{Neat}$ cm$^{-1}$: 3500(OH), 1605, 1595(Ar).

According to a similar procedure to the above experiment (1), 16β(3-butenyl)-estradiol 3-methylether is produced from 16-ketoestradiol 3-methylether and 3-butenylmagnesium bromide. IR $\nu_{max}^{Neat}$ cm$^{-1}$: 3500(OH), 1635(c=c), 1605, 1590(Ar). Mass: m/e 340(M$^+$), 325(-15), 322(-18).

(2) According to a similar manner to Example 2, 16β-n-butylestradiol 3-methylether is reacted with methylmagnesium iodide gives 16β-n-butylestradiol melting at 148 to 150° C (recrystallization from hexane).

IR $\nu_{max}^{KBr}$ cm$^{-1}$: 3400(OH), 1605(Ar).

Elemental analysis for C$_{22}$H$_{32}$O$_2$: Calcd. C, 80.44; H, 9.83. Found C, 80.40; H, 9.99.

In a similar manner to above experiment (2), 16β-(3-butenyl)-estradiol is obtained from 16β(3-butenyl)-estradiol 3-methylether. Melting point: 154° to 156° C. IR $\nu_{max}^{KBr}$ cm$^{-1}$: 3400(OH), 3050, 1635(c=c), 1605(Ar)

Elemental analysis for C$_{22}$H$_{30}$O$_2$ Calcd. C, 80.93; H, 9.26. Found C, 80.62; H, 9.58.

What we claim is:

1. A compound of the formula

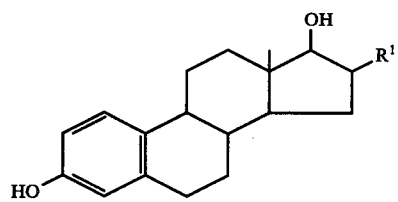

wherein R$^1$ is an alkyl group of two to four carbon atoms, allyl, or 3-butenyl.

2. A compound as claimed in claim 1, which is 16β-ethylestradiol.

3. A compound as claimed in claim 1, which is 16β-isopropylestradiol.

4. A compound as claimed in claim 1, which is 16β-allylestradiol.

5. A compound as claimed in claim 1, which is 16β-n-butylestradiol.

6. A compound as claimed in claim 1, which is 16β-(3-butenyl)-estradiol.

7. A pharmaceutical composition comprising a compound as claimed in claim 1 together with a pharmaceutically acceptable carrier or diluent therefor.

8. A method for producing a compound of the formula: (I)

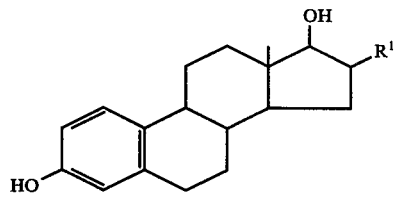

wherein R$^1$ is an alkyl group of two to four carbon atoms, allyl or 3-butenyl, which comprises reacting a compound of the formula (II)

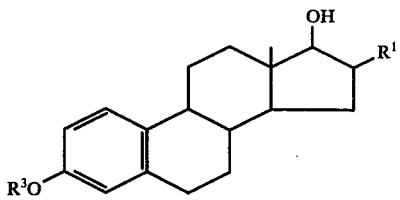

wherein R$^1$ has the same meaning as defined above and R$^3$ is an alkyl group of one to three carbon atoms, phenyl or p-nitrophenyl, with a reagent selected from the group consisting of hydrohalogenic acids; halides of phosphorus, boron, aluminum, thallium or titanium; pyridinium halides; Grignard reagents; and sodium iodide-dimethylsulfoxide at a temperature of −10° to 250° C.

9. A method for producing a compound of the formula: (I)

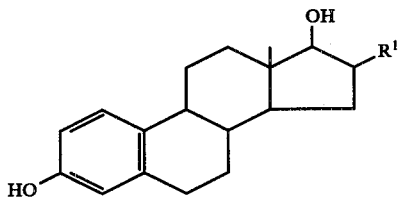

wherein $R^1$ is an alkyl group of two to four carbon atoms, allyl or 3-butenyl, which comprises subjecting a compound of the formula:

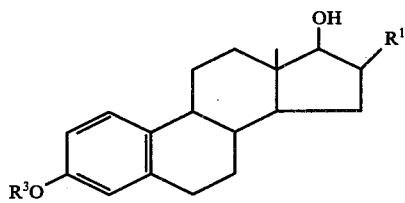
(II)

wherein $R^1$ has the same meaning as defined above and $R^3$ is benzyl or benzhydryl, to catalytic reduction in the presence of platinum oxide, palladium or Raney nickel at 10° to 60° C at a pressure of 1 to 100 kg/cm², or subjecting the compound of the formula (II) to hydrolysis in the presence of a hydrohalogenic acid; a halide of phosphorus, boron, aluminum, thallium or titanium; a pyridinium halide; a Grignard reagent; sodium iodide-dimethylsulfoxide; or a halogenoacetic acid.

10. A method for producing a compound of the formula:

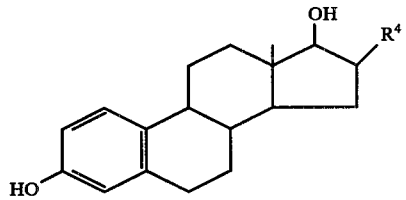

wherein $R^4$ is an alkyl group of two to four carbon atoms, allyl or 3-butenyl, which comprises subjecting a compound of the formula:

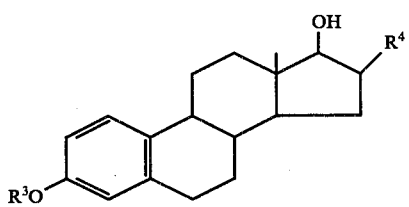

wherein $R^4$ has the same meaning as defined above and $R^3$ is an alkylcarbonyl group, of which the alkyl moiety has one to three carbon atoms, benzoyl or phenylpropionyl, to hydrolysis in the presence of an alkali metal hydroxide, alkali metal carbonate, alkali metal hydrogen carbonate, triethylamine, triethylenediamine, hydrochloric acid, sulfuric acid, nitric acid, phosphoric acid, formic acid, acetic acid, oxalic acid or p-toluenesulfonic acid, at 0° to 80° C.

11. A method as claimed in claim 8, wherein from 1 to 10 moles of said reagent per mole of compound (II) is used.

12. A method as claimed in claim 8, wherein said reaction is conducted without a solvent.

13. A method as claimed in claim 8, wherein said reaction is conducted in a solvent selected from the group consisting of ethers, halogenated hydrocarbons, esters, nitrobenzene, dimethyl formamide, dimethyl sulfoxide, and tetramethylphosphoramide, at a temperature of from −10° C to the boiling point of said solvent.

14. A method as claimed in claim 9, wherein said catalytic reduction is conducted in a solvent selected from the group consisting of methanol, ethanol, ether, and tetrahydrofuran.

15. A method as claimed in claim 10, wherein said hydrolysis is conducted in a solvent comprising water and a member of the group consisting of alkanols having 1 to 4 carbon atoms, ether, ethyl acetate, tetrahydrofuran, dimethyl sulfoxide and dimethyl formamide.

* * * * *

UNITED STATES PATENT OFFICE
CERTIFICATE OF CORRECTION

Patent No. 4,082,780　　　　　　　　Dated April 4, 1978

Inventor(s) Takuichi Miki, et al

It is certified that error appears in the above-identified patent and that said Letters Patent are hereby corrected as shown below:

Column 1, line 33: "than" should be --have--.

Column 5, line 44: "per se" should be --per se--.

Column 9, line 44: "16$\beta$ -n-" should be --16$\alpha$ -n- --.

Signed and Sealed this

*Twenty-first* Day of *November 1978*

[SEAL]

Attest:

RUTH C. MASON
*Attesting Officer*

DONALD W. BANNER
*Commissioner of Patents and Trademarks*